(12) United States Patent
Gordon et al.

(10) Patent No.: US 6,491,805 B1
(45) Date of Patent: Dec. 10, 2002

(54) SAMPLE-ANALYSIS SYSTEM WITH ANTISYNCHRONOUSLY DRIVEN CONTACTLESS CONDUCTIVITY DETECTOR

(75) Inventors: Gary B. Gordon, Saratoga, CA (US); Tom A. van de Goor, Foster City, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/576,690

(22) Filed: May 23, 2000

(51) Int. Cl.[7] ............... G01N 27/453; G01N 27/04; G01R 27/22
(52) U.S. Cl. .............. 204/603; 204/612; 204/409; 422/82.02
(58) Field of Search ............... 204/450–452, 204/461, 549, 600, 603, 612, 645, 409; 422/82.02

(56) References Cited

PUBLICATIONS

Kaniansky et al. ("Contactless conductivity detection in capillary zone electrophoresis", Journal of Chromatography A, 844 (1999) 349–359). Month unknown.
Gas et al. ("High–frequency Contactless Conductivity Detection in Isotachophoresis", Journal of Chromatography, 192 (1980, May) 253–257).
Jose A Fracassi da Silva & Claudimir L. do Lago "An Oscillometric Detector for Capillary Electrophoresis", *Analytical Chemistry*, vol. 70, 1998, pp. 4339–4343. Oct.
Jiri Vacik, Jiri Zuska & Iva Muselasova, "Improvement of the Peformance of a High–Frequency Conductivity Detector for Isotachophoresis" Journal of Chromatography, 17,322, 1985, 5 pages. Month unknown.
Andress J. Zemann, Erhard Schnell, Dietmar Volger, & Glnther K. Bonn, "Contactless Conductivity Detection for Capillary Electrophoresis" Analytical Chemistry, V. 70, 1998, pp. 563.567. Feb. 2.

*Primary Examiner*—T. Tung
*Assistant Examiner*—Alex Noguerola

(57) ABSTRACT

In a differential condition, an electrophoresis system antisynchronously drives a longitudinally-separated pair of contactless drive electrodes, both of which are coupled to a detection electrode through a separation channel. In this condition, the system provides a series of peaks readout in ITP-separation mode. In a direct condition, the system antisynchronously drives a pair of drive electrodes, only one of which is coupled to the detection electrode through the channel; the other is coupled to the detection electrode but not though the channel. In this condition, the system provides a series of peaks readout in CZE mode. In either case, the antisynchronous drive enhances the detection signal by canceling at the detection electrode signal components associated with the AC drive source. Similar advantages are achieved for a capillary differential electrophoresis system and for a planar direct electrophoresis system.

11 Claims, 4 Drawing Sheets

SAMPLE-ANALYSIS SYSTEM WITH ANTISYNCHRONOUSLY DRIVEN CONTACTLESS CONDUCTIVITY DETECTOR

BACKGROUND OF THE INVENTION

The present invention relates to analytical chemistry and, more particularly, to conductivity detectors for electrophoresis and other analysis methods using sample flow channels. A major objective of the invention is to provide for improved contactless conductivity detection for electrophoretically separated sample components.

Much of modern progress in the medical, environmental, forensic, and other sciences can be attributed to advances in analytical chemistry. One important class of analytical tools separates sample components by moving them at different rates along a separation channel. Of primary interest herein is electrophoresis in which an electric field moves sample components along a separation channel; the components are separated according to their electrophoretic mobilities (roughly corresponding to charge-to-mass ratios).

There are two prevalent types of electrophoresis. In capillary zone electrophoresis (CZE) a sample is dissolved in an otherwise uniform buffer. A constant voltage potential is applied along the separation channel so that ions move at rates corresponding to their electrophoretic mobilities. Since different ionic species have different charge-to-mass ratios, they separate as they migrate along the channel.

In isotachophoresis (ITP), the separation channel is initially filled by a "leading" buffer, with the sample introduced at one end of the channel. An electric potential gradient along the channel causes the sample ions to migrate according to their electrophoretic mobilities. As the sample moves along the channel, it is followed by a trailing buffer having a lower electrophoretic mobility than the leading buffer. Sample components with intermediate electrophoretic mobilities remain between the buffers, forming into adjacent bands.

Once the sample components are separated it is usually desirable to identify and, perhaps, quantify the components. This typically requires detection of the components. Detectors are available that detect components by monitoring certain parameters, such as conductivity, fluorescence or absorption of ultra-violet (UV) electromagnetic energy as sample components pass.

Conductivity detection is appealing for electrophoresis since it operates on the same parameter used to separate the components. In other words, sample components that cannot be detected by monitoring conductivity are those unlikely to be separated by electrophoresis. Separated components necessarily have a measurable conductivity associated with their electrophoretic mobilities.

Contact conductivity detection can be implemented by locating electrodes on the interior channel walls of an electrophoretic channel. Typically, electrodes can oppose each other across a transverse width or diameter of the electrophoretic channel. An alternating current can be applied to a drive electrode, while the potential at a detection electrode (arranged as an intermediate node in a voltage divider) can be monitored to provide an indication of sample conductivity. However, since the electrodes are in contact with the sample fluid, chemical reactions at the electrodes can affect both the electrodes and the sample. Such interaction can cause undesirable artifacts within a run and undermine repeatability between runs.

Contactless conductivity detection typically involves forming electrodes on the outside walls that define the electrophoresis channel. Electrodes can be electrically coupled (i.e., an electrical signal on one can be detected by the other) to each other through the channel. Since the sample does not contact the electrodes, the problem of chemical interaction between sample and electrodes is effectively addressed.

Changes in sample conductivity as components pass the electrodes cause changes in impedance between the electrodes. This impedance can be monitored using a voltage divider arrangement. However, the impedance variations are relatively small due to the constant capacitance contribution of the channel walls to the impedance. Small signal-to-background ratios result in reduced sensitivity to conductivity changes. The output gain of the detector can be increased to amplify the effect of conductivity changes on the detector output. However, undesirable artifacts, such as variations in the AC drive amplitude due to power source fluctuations, are amplified as well.

There are further problems in the case of isotachophoresis. The conductivity profile of a typical sample separated by isotachophoresis is a step function. This means that the background signal increases as the sample component bands progress past the detector. This further reduces the signal-to-background ratio of the detector output.

Finally, the contributions of individual sample components are not readily read from a step function. A more readable function is obtained by differentiating the step function to obtain a profile of the rate of conductivity change over time. This produces a relatively readable series of peaks at the boundaries between component bands. However, the mathematical differentiation introduces an additional step in the procedure and introduces computation errors into the final data.

What is needed is a conductivity detector that is more sensitive than the foregoing contactless conductivity detectors, but more reliable than foregoing contacting conductivity detectors. Furthermore, in the case of isotachophoresis, the problems with the step function should be addressed.

SUMMARY OF THE INVENTION

The present invention provides sample-analysis systems with antisynchronously driven contactless conductivity detectors. The invention has particular applicability to electrophoresis because of its amenability to conductivity detection. However, in its most general aspect, the invention is not dependent on the separation technology.

The sample-analysis system includes a sample-component separator and a sample-component detector. The separator provides a channel along which sample components move past the detector. The detector includes an AC source, at least two drive electrodes, at least one detection electrode, and a signal processor. The AC source drives two drive electrodes antisynchronously (180°+/−45° out of phase, the closer to 180° the better). A detection electrode is electrically coupled to both drive electrodes so that the drive signals tend to cancel; the degree of cancellation varies according to the local conductivity in the separation channel. The signal processor provides a readout that represents the degree of cancellation, and thus conductivity.

So that conductivity changes can be detected, at least one drive electrode is electrically coupled to the detection electrode through the separation channel. In differential realizations of the invention, both antisynchronously driven electrodes are coupled to the detection through the channel, while in direct realizations of the invention, one of the antisynchronously driven electrodes is electrically coupled to the detection electrode but not through the channel. The direct realizations provide a direct readout of local conductivity, while the differential realizations provide a direct readout of changes in local conductivity. Accordingly, the direct realizations provide a desired "series-of-peaks" readout for CZE, while the differential realizations provide a "series-of-peaks" readout for ITP. The direct realization provides superior spatial resolution, while the differential realization provides superior background signal cancellation.

The invention provides for hybrid-detection analytical systems that implement both differential and direct detector modes. For example, three drive electrodes can be used, two of which are coupled to the detection electrode through a separation channel, and one of which is coupled to the detection electrode but not through the separation channel. A switch can be used to select whether the AC power source is coupled for differential detection or direct detection. Such hybrid-detection systems can provide a desired series-of-peaks readout for both CZE and ITP separations by respectively selecting direct and differential detection modes.

The non-hybrid differential and direct systems can also provide the desired series-of-peaks readouts in either CZE or ITP mode. In a direct detection system, the signal processor can include a differentiator to provide a series-of-peaks readout for ITP separations. In a differential detection system, the signal processor can include an integrator to provide a series-of-peaks readout for CZE separations.

The invention provides for a variety of geometries. In planar configurations, the detection electrode or electrodes can be coupled to drive electrodes transversely of a longitudinally extending separation channel. Alternatively, detection electrodes and drive electrodes can all be formed on the same side of a separation channel; in this case, shielding can be used to prevent undesired electrical bypassing of the separation channel. In a capillary separation channel configuration, electrodes can be formed as annular rings on the exterior of the capillary. In this case, a detection electrode can be disposed longitudinally between drive electrodes.

The present invention provides for an enhanced detection signal by canceling drive signal components. This cancellation removes artifacts due to AC source voltage variations and provides more sensitive detection of conductivity variations. The invention also provides for desired series-of-peaks readouts for both CZE and ITP separations. These and other features and advantages of the invention are apparent from the description below with reference to the following drawings.

DESCRIPTION OF THE PREFERRED EMBODIMENTS

Figure 1:
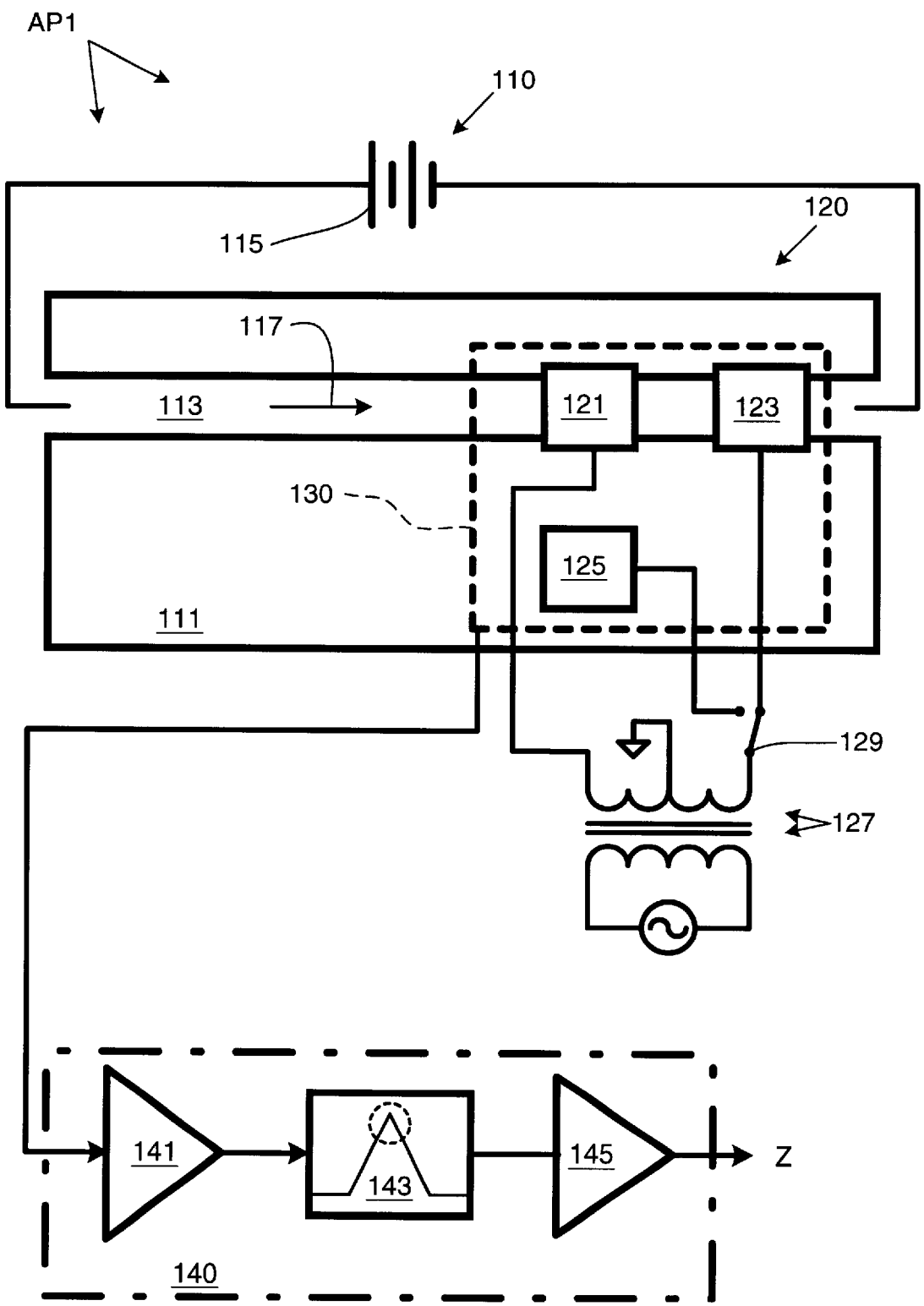
FIG. 1 is a schematic view of a planar electrophoresis system with a hybrid direct/differential antisynchronously driven contactless conductivity detector in accordance with the present invention.
Figure 2:
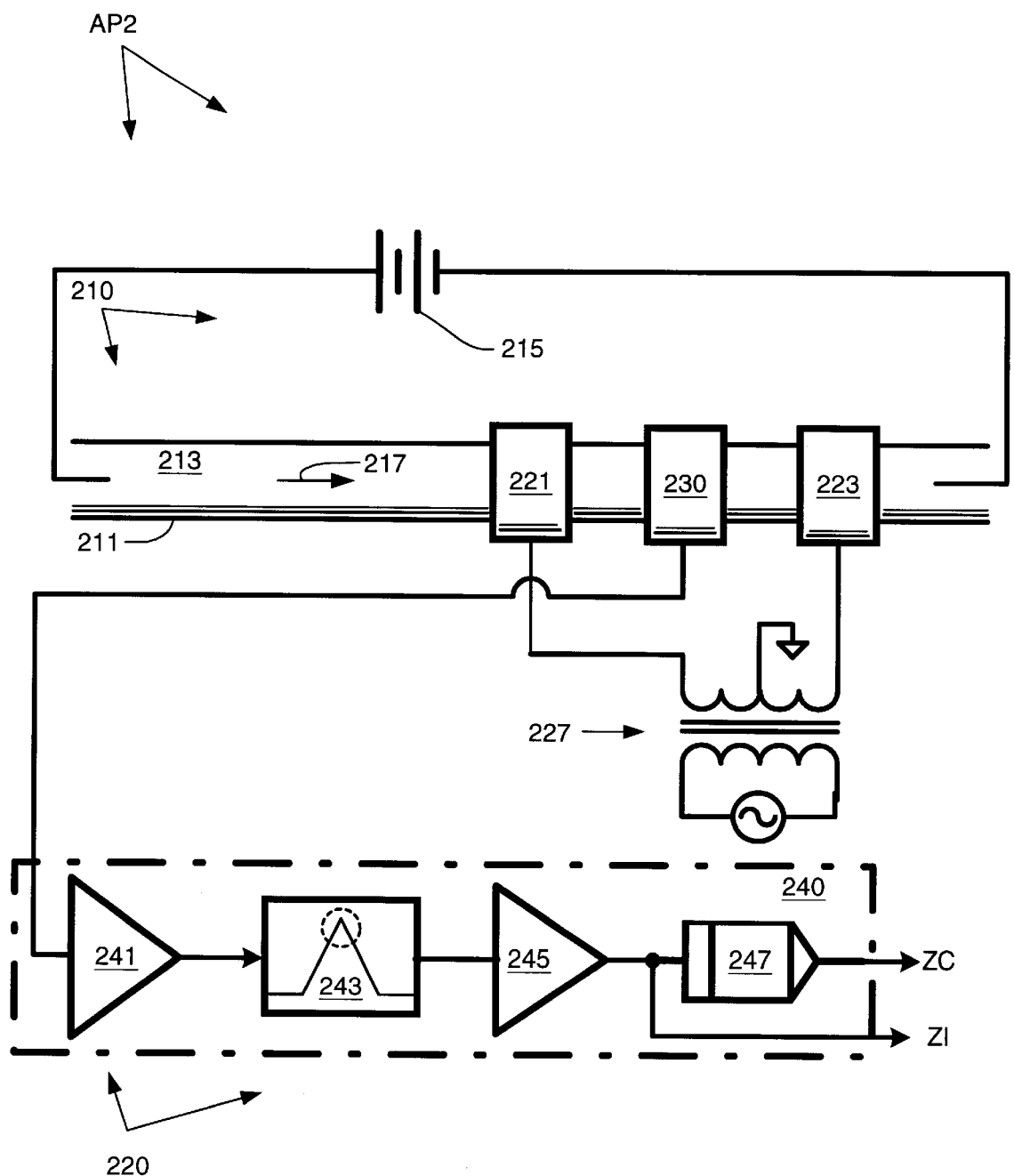
FIG. 2 is a schematic plan view of a capillary electrophoresis system with a differential antisynchronously driven contactless conductivity detector in accordance with the present invention.
Figure 3:
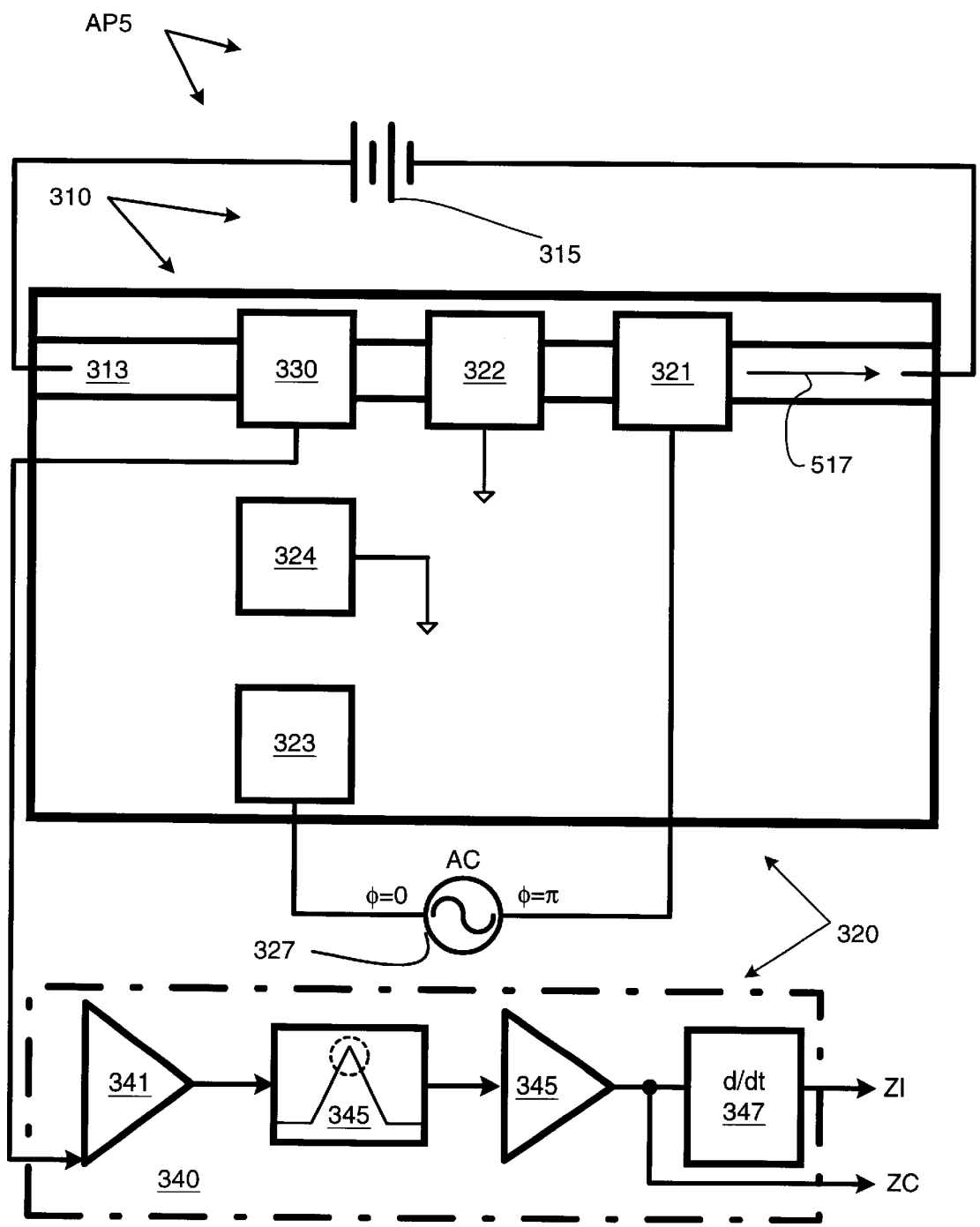
FIG. 3 is a schematic plan view of a planar electrophoresis system with a direct antisynchronously driven shielded contactless conductivity detector in accordance with the present invention.
Figure 4:
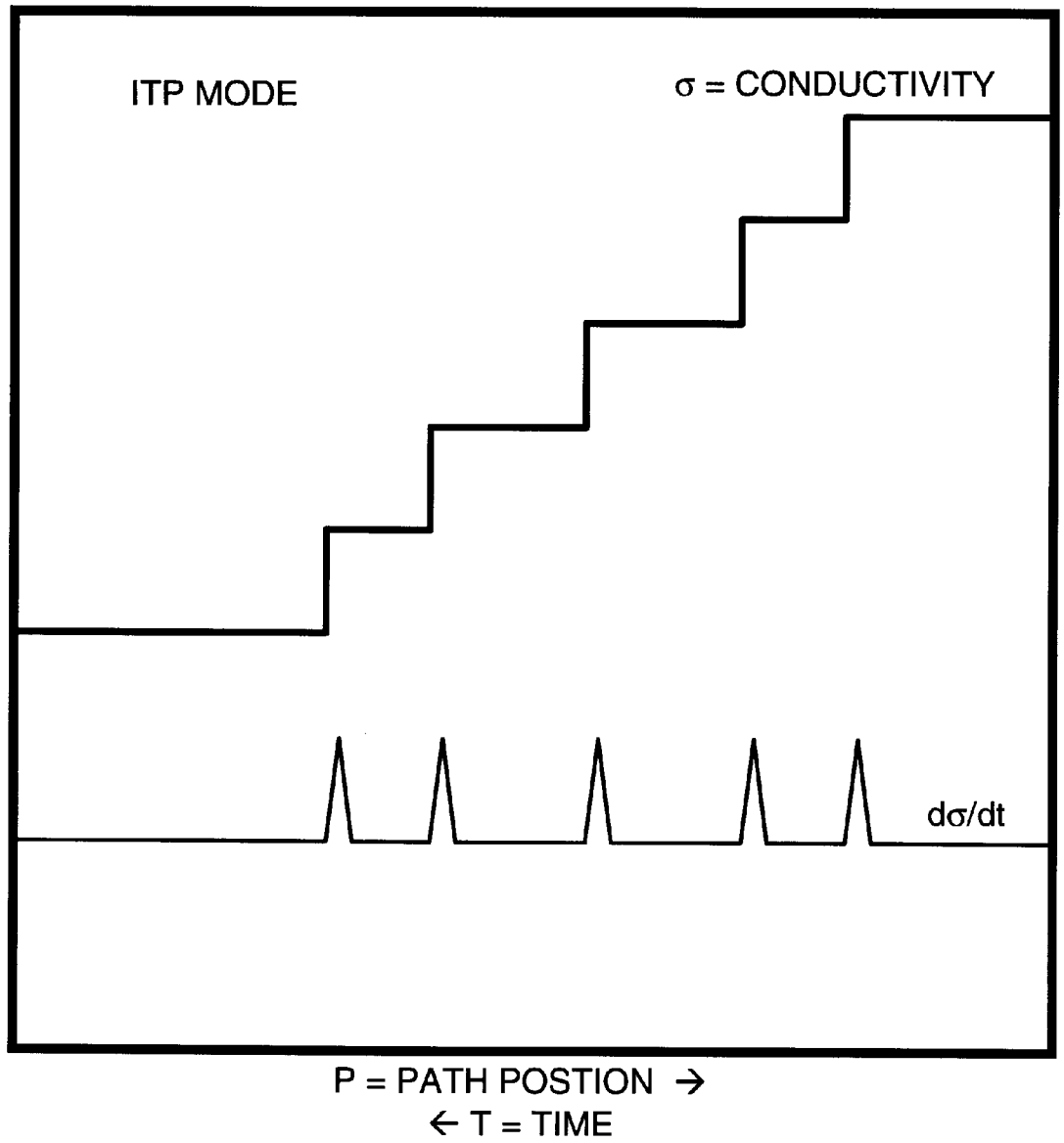
FIG. 4 is a graph showing a conductivity profile and a conductivity differential profile for an ITP separation by the systems of FIGS. 1, 2 and 3.

The present invention provides for antisynchronously driven contactless conductivity detection as exemplified in electrophoresis system AP1 of FIG. 1, electrophoresis system AP2 of FIG. 2, and electrophoresis system AP3 of FIG. 3. All three systems provide for CZE and ITP modes of operation with a series-of-peaks readout in each mode. A series of peaks readout for ITP mode is shown in FIG. 4 as $d\sigma/dt$ where "$\sigma$" is the symbol for conductivity.

As shown in FIG. 1, electrophoresis system AP1 includes a sample-component separator 110 and a sample-component detector 120. Separator 110 can operate in ITP and CZE separation modes, while detector 120 can operate in differential and direct detection modes. To achieve a series-of-peaks readout, the direct detection mode can be used with CZE separation mode, and the differential detection mode can be used with ITP separation mode.

Separator 110 includes a polyimide assembly 111, which is a covered substrate. A separation channel 113 is formed as a groove in the substrate of assembly 111. A DC power supply 115 urges sample and buffer fluid to flow in channel 113 in the direction indicated by arrow 117 at rates determined by respective electrophoretic mobilities. A fluid handling system supplies buffer to channel 113 and handles the effluent.

Detector 120 includes drive electrodes 121, 123, and 125, a two-phase transformer-coupled AC power supply 127, a detection-mode switch 129, a detection electrode 130, and a signal processor 140. Signal processor 140 provides the detector readout Z. To this end, signal processor 140 includes an AC amplifier 141, a peak detector 1, and a DC (low-frequency) amplifier 145.

In ITP separation mode, channel 113 is initially filled with a high-electrophoretic-mobility lead buffer. Sample is injected into the channel input (left side). Power supply 115 applies a potential along with channel. This draws the lead buffer longitudinally along channel 113 towards its (right) end. Sample components follow the lead buffer, and the volume vacated by the components is progressively filled with a low-electrophoretic-mobility buffer.

Sample components with electrophoretic mobilities between those of the buffers remain between the buffers as the electrophoretic channel contents migrate along the channel. These components separate into adjacent bands. Conductivity correlates positively with electrophoretic mobility; accordingly, the conductivity of the sample components along with the leading and trailing buffers is represented by the step function $\sigma$ of FIG. 4.

Detection-mode switch 129 is preferably in its differential condition for ITP separation mode. In its differential condition as shown in FIG. 1, switch 129 couples AC power supply 127 to electrodes 121 and 123 to drive them antisynchronously, while electrode 125 is decoupled from the drive signals.

Electrodes 121 and 123 are coupled to detection electrode 130 through channel 113 at respective longitudinal positions thereof. The gains of electrical signals received by detection electrode 130 from drive electrodes 121 and 123 are determined in part by the conductivities of the intervening fluid. If the conductivities are the same, as they are when there are no band boundaries in the longitudinal range spanned by drive electrodes 121 and 123, the detection signals cancel at detection electrode 130. Complete cancellation results in a zero readout Z from signal processor 140.

As a band boundary moves under drive electrode 121, the average conductivity between drive electrode 121 and detection electrode 130 goes down, while the conductivity between drive electrode 123 and detection electrode 130 remains the same. Thus, the signal from drive electrode 123 dominates and the cancellation at detection electrode 130 is incomplete. As a result, signal processor 140 receives an AC signal of increasing amplitude from detection electrode 130.

AC amplifier 141 amplifies this AC signal. Peak detector 143 determines the peak level of the amplified AC signal. The peak detection signal is amplified by DC amplifier 145, which provides detector readout Z. Readout Z increases as a band boundary moves past drive electrode 121, reaching a peak when the sample-component boundary is between drive electrodes 121 and 123. The readout decreases as the band passes by drive electrode 123. Over a series of bands, readout Z assumes the desired series-of-peaks form shown in FIG. 4 as $d\sigma/dt$.

In system AP1, channel 113 is 100 microns ($\mu$m) in width and depth. Drive electrodes 121, 123, 125 are 120 $\mu$m squares. The spacing between drive electrode 121 and drive electrode 123 is 120 $\mu$m, so the differential-detection-mode range for detector 120 is 360 $\mu$m. The spacing between drive electrode and drive electrode 125 is also 120 $\mu$m. However, since drive electrode is not located along channel 113 (and thus is not electrically coupled to detection electrode 130 through channel 113), the direct-detection-mode detection range is only 120 $\mu$m.

More generally, the electrode spacing should be on the order of the electrophoretic channel transverse dimensions. "On the order of" can be taken herein to mean one-half ($\times\frac{1}{2}$) to five times ($\times 5$) the average transverse dimension of the electrophoresis channel. Greater spacings can reduce crosstalk, but reduce resolution. Smaller spacings can yield higher resolution with a cost of lower sensitivity due to cross-talk between the drive electrodes. On the other hand, proper shielding can reduce cross-talk. In general, the drive electrodes should be no further apart than the minimum length band so that only one band interface is between the drive electrodes at any given time.

When system API is CZE separation mode, mode switch 129 is preferably in its "direct condition", coupling drive electrode 125 to AC power supply 127 and decoupling drive electrode 123. Peak amplitude variations associated with imperfect regulation of AC power supply 127 are cancelled. When only buffer is in the region of channel 113 near drive electrode 121, the result is a fixed amplitude AC signal from detection electrode 113. Preferably, in this situation, the fixed amplitude is zero, but if it is not, a zero readout Z can be achieved by biasing DC amplifier 145.

When a sample-component peak passes drive electrode 121, the conductivity between it and detection electrode 130 increases. The signal received by detection electrode 130 from drive electrode 121 thus strengthens. On the other hand, the signal received by detection electrode 130 from drive electrode 125 remains unchanged (since the latter is not coupled to channel 113). Thus, there is a net change in the amplitude of the AC signal received by signal processor 140 from detection electrode 130, and this is reflected by a level increase in readout signal Z. Readout signal Z reaches a maximum when the component peak is centered on drive electrode 121, and then decreases. Roughly speaking, when in CZE separation mode plus direct detection mode, readout signal Z provides a series of peaks readout matching the sample concentration distribution moving along channel 113.

In summary, when system API is in ITP separation mode, detector 120 can operate differentially (comparing conductivities at two channel positions) to provide a series-of-peaks readout; when system API is in CZE separation mode, detector 120 can operate in direct detection mode to provide a series-of-peaks readout indicating conductivity variations over time. It is possible for detector 120 to operate in direct detection mode when system AP1 is in ITP separation mode to take advantage of the higher resolution; in that case, readout Z takes the form of a step function, as indicate by Z=$\sigma$ in FIG. 4. Detector 120 can also operate in differential detection mode when system API is in CZE separation mode.

It should be noted that detection electrode 130 spans the three areas respectively spanned by drive electrodes 121, 123, and 125. Similar functionality can be achieved by using three detection electrodes, each opposing a respective drive electrode. In this case, the detection electrodes can be shorted to function as a single electrode. Herein, a shorted assembly of electrodes is considered a single electrode.

A second electrophoresis system AP2 comprises a capillary electrophoresis separation system 210 and a detector 220, as shown in FIG. 2. In system AP2, a capillary tube 211 defines a separation channel 213; under the electric field imposed by DC power supply 215, sample components move in the direction indicated by arrow 217. In particular, detection electrode 230 is located longitudinally between drive electrodes 221 and 223 on capillary tube 211. Each electrode 221, 223, 230 is an annular aluminum ring formed on the exterior wall of capillary tube 211. The lengths and spacings of the electrodes are all 100 $\mu$m, equal to the capillary channel diameter.

An inductively coupled AC power supply 227 provides complementary AC drive waveforms to drive electrodes 221 and 223. These waveforms induce corresponding waveforms in detection electrode 230. The induced detection waveforms partially or completely cancel each other at detection electrode 230, depending on the relative conductivities between detection electrode 230 and each of drive electrodes 221 and 223.

The detection waveform is processed by analog signal processor 240, which includes AC amplifier 241, peak detector 243, DC amplifier 245, and integrator 247 (a low frequency filter), to provide outputs ZC and ZI. Output ZI provides a peak form output for ITP mode, while output ZC provides a peak form output for CZE mode.

In ITP mode, output ZI is at zero while electrodes 221, 223, and 230 are within the same sample component band. With system AP3 in ITP mode, output ZI changes while a sample-component boundary is progressing between electrodes. When the boundary is centered below detection electrode 230, output ZI is at a peak. As with system AP1, the outputs of system AP2 in ITP mode are represented in FIG. 4, with ZC=$\sigma$, and ZI =$d\sigma/dt$.

A planar quasi-balanced direct electrophoresis system AP3 is shown in FIG. 3. For economy and easy of manufacturing, all electrodes are formed on the same surface. To avoid unwanted electrical coupling along the surface, shielding is interposed.

System AP3 includes a separator 310 and a detector 320. Separator 310 includes an electrophoresis channel 313 formed in a polyimide assembly 311 and a DC power supply 515. Flow along channel 313 is in the direction indicated by arrow 317.

Detector 320 includes an inductively coupled AC power supply 327, drive electrodes 321 and 323, shield electrodes 322 and 324, a detection electrode 330, and a detection signal processor 340. Signal processor 340 includes an AC amplifier 341, a peak detector 343, a DC amplifier 345, and a differentiator 347. DC amplifier 345 provides a series-of-peaks readout for CZE mode, while differential 347 provides a series-of-peaks readout for ITP mode.

Drive electrode 321 is over channel 313, while drive electrode 323 is not. As detection electrode 330 is on the same surface as drive electrodes 321 and 323, there is a potential for electrical energy to couple to detection electrode 330 from drive electrodes 321 and 323 without passing through substrate 511 or channel 513. To limit this spurious coupling, ground electrodes 322 and 324 are interposed between detection electrode 330 and respective drive electrodes 321 and 323.

The invention provides for electrophoresis systems with dual CZE and ITP mode operation and for systems dedicated to one mode or the other. Various configurations, dimensions, and spacings of electrodes are provided for. Different numbers, geometries and arrangements of drive, detection, and shielding electrodes can be used. Different drive and processing circuitry can be used. For examples, RMS detectors or envelope followers can be used instead of the peak detectors. While the illustrated embodiments have two drive electrodes and one detection electrode, the inventions provides for greater numbers of electrodes. For the purposes of the claims, plural electrodes shorted together constitute a single electrode. While the conductivity detectors are shown in the context of electrophoresis systems, the detectors can be used for detecting components separated by other means. These and other variations upon and modifications to the illustrated embodiments are provided for by the invention, the scope of which is defined by the following claims.

What is claimed is:

1. A sample-analysis system comprising:
   a separator for separating sample components as they move along a longitudinally extending channel, said separator including said channel;
   a detector for detecting sample components moving along said channel, said detector including:
      a detection electrode capacitively coupled to said channel;
      longitudinally separated first and second drive electrodes, said first drive electrode being electrically coupled to said detection electrode through said channel;
      drive means for driving said first and second drive electrodes antisynchronously, said drive means being electrically coupled to said drive electrodes; and
      a signal processor for providing a readout signal representing the contents of said channel as said sample components move past said detection-electrode set.

2. A sample-analysis system as recited in claim 1 wherein said second drive electrode is coupled to said detection electrode through said channel.

3. A sample-analysis system as recited in claim 2 wherein said separator includes an ITP mode in which sample components are separated by isotachophoresis, said signal processor providing said readout signal as a series of peaks when said separator is in said ITP mode.

4. A sample-analysis system as recited in claim 3 wherein said separator includes a CZE mode in which sample components are separated by chemical-zone electrophoresis, said signal processor including an integrator for providing said readout signal as a series of peaks when said separator is in said CZE mode.

5. A sample-analysis system as recited in claim 1 wherein said detection electrode is disposed longitudinally between said first and second drive electrodes.

6. A sample-analysis system as recited in claim 1 wherein said detection electrode is spaced from said first drive electrode transversely by said channel.

7. A sample-analysis system comprising:
   a separator for separating sample components as they move along a longitudinally extending channel, said separator including said channel, said separator providing an ITP mode in which sample components are separated by isotachophoresis; and
   a detector for detecting sample components moving along said channel, said detector including
      a detection electrode capacitively coupled to said channel,
      first and second drive electrodes, said first drive electrode being electrically coupled to said detection electrode through said channel,
      drive means for driving said first and second drive electrodes antisynchronously, said drive means being electrically coupled to said drive electrodes,
      a signal processor for providing a readout signal representing the contents of said channel as said sample components move past said detection-electrode set, said signal processor providing said readout signal as a series of peaks when said separator is in said ITP mode,
      a third electrode electrically coupled to said detection electrode but not through said channel, and
      a switch having differential and direct conditions, said switch when in said differential condition coupling said drive means to said first and second drive electrodes to drive them antisynchronously, said switch when in said direct condition coupling said drive means to said first and third drive electrodes to drive them antisynchronously.

8. A sample-analysis system as recited in claim 7 wherein said separator includes a CZE mode in which sample components are separated by chemical-zone electrophoresis, whereby
   when said separator is in said CZE mode and said switch is in said direct condition, said signal processor provides a series-of-peaks readout in which the peaks represent sample component peaks, and
   when said separator is in said ITP mode and said switch is in said differential condition, said signal processor provides a series-of-peaks readout in which the peak represent boundaries between sample-component bands.

9. A sample-analysis system comprising:
   a separator for separating sample components as they move along a longitudinally extending channel, said separator including said channel;
   a detector for detecting sample components moving along said channel, said detector including
      a detection electrode capacitively coupled to said channel,
      first and second drive electrodes, said first drive electrode being electrically coupled to said detection electrode through said channel, said second drive electrode being electrically coupled to said detection electrode but not through said channel, drive means for driving said first and second drive electrodes antisynchronously, said drive means being electrically coupled to said drive electrodes, and a signal processor for providing a readout signal representing the contents of said channel as said sample components move past said detection-electrode set.

10. A sample-analysis system as recited in claim 9 wherein said separator includes a CZE mode in which sample components are separated by chemical-zone electrophoresis, said signal processing means providing said readout signal as a series of peaks when said separator is in said CZE mode.

11. A sample-analysis system as recited in claim 10 wherein said separator includes an ITP mode in which sample components are separated by isotachophoresis, said signal processing means including a differentiator for providing said readout signal as a series of peaks when said separator is in said ITP mode.

* * * * *